US010244332B2

United States Patent
Lineaweaver et al.

(10) Patent No.: US 10,244,332 B2
(45) Date of Patent: Mar. 26, 2019

(54) DEVICE MONITORING FOR PROGRAM SWITCHING

(71) Applicant: Cochlear Limited, Macquarie University (AU)

(72) Inventors: Sean Lineaweaver, Gig Harbor (AU); John Michael Heasman, Hampton (AU)

(73) Assignee: Cochlear Limited, Macquarie University (AU)

( * ) Notice: Subject to any disclaimer, the term of this patent is extended or adjusted under 35 U.S.C. 154(b) by 16 days.

(21) Appl. No.: 15/165,544

(22) Filed: May 26, 2016

(65) Prior Publication Data
US 2017/0215010 A1     Jul. 27, 2017

Related U.S. Application Data

(60) Provisional application No. 62/286,626, filed on Jan. 25, 2016.

(51) Int. Cl.
*H04R 25/00* (2006.01)
*A61N 1/378* (2006.01)
*A61N 1/36* (2006.01)

(52) U.S. Cl.
CPC ....... *H04R 25/305* (2013.01); *A61N 1/36036* (2017.08); *A61N 1/378* (2013.01); *H04R 25/554* (2013.01); *H04R 2225/33* (2013.01)

(58) Field of Classification Search
CPC ............... H04R 25/305; H04R 25/554; H04R 2225/33; A61N 1/3032; A61N 1/378
USPC .......................................... 381/312–321, 60
See application file for complete search history.

(56) References Cited

U.S. PATENT DOCUMENTS

| | | | |
|---|---|---|---|
| 5,271,397 A * | 12/1993 | Seligman | A61N 1/36036 607/137 |
| 5,524,150 A | 6/1996 | Sauer | |
| 6,711,271 B2 * | 3/2004 | Hou | H04R 25/00 381/312 |
| 7,120,500 B1 * | 10/2006 | Seligman | A61N 1/378 607/55 |
| 7,315,626 B2 | 1/2008 | Pedersen | |
| 8,483,416 B2 | 7/2013 | Roeck et al. | |
| 8,538,049 B2 | 9/2013 | Apfel et al. | |
| 9,781,521 B2 * | 10/2017 | Kofod-Hansen | H04R 25/305 |
| 2005/0254676 A1 * | 11/2005 | Rass | H04R 25/558 381/312 |

(Continued)

*Primary Examiner* — Sunita Joshi
(74) *Attorney, Agent, or Firm* — Edell, Shapiro & Finnan, LLC (57) ABSTRACT

A method for operating a hearing prosthesis including operating the hearing prosthesis in a first mode, and monitoring an operating characteristic of the hearing prosthesis. The operating characteristic may relate to one or more of a power supply configured to provide power to the hearing prosthesis, or a temperature characteristic of the hearing prosthesis. The method also includes determining that the operating characteristic is at a threshold level, and responsive to determining that the operating characteristic is at the threshold level, operating the hearing prosthesis in a second mode. In this example, operating the hearing prosthesis in the second mode at least one of uses less power or generates less heat than operating the hearing prosthesis in the first mode.

20 Claims, 5 Drawing Sheets (56) References Cited

U.S. PATENT DOCUMENTS

| | | | |
|---|---|---|---|
| 2006/0080087 A1* | 4/2006 | Vandali | A61N 1/36032 704/207 |
| 2008/0123882 A1* | 5/2008 | Bauml | H04R 25/305 381/312 |
| 2009/0074215 A1* | 3/2009 | Schumaier | H04R 25/70 381/314 |
| 2012/0223590 A1* | 9/2012 | Low | H02J 5/005 307/104 |
| 2013/0259278 A1 | 10/2013 | Kill et al. | |
| 2013/0272556 A1* | 10/2013 | Hamacher | H04R 25/305 381/328 |
| 2013/0343584 A1* | 12/2013 | Bennett | H04R 25/554 381/315 |

\* cited by examiner

DEVICE MONITORING FOR PROGRAM SWITCHING

CROSS-REFERENCE TO RELATED APPLICATION

This application claims priority to U.S. Provisional Patent Application No. 62/286,626 filed on Jan. 25, 2016, the entirety of which is incorporated herein by reference.

BACKGROUND

Various types of hearing prostheses provide persons with different types of hearing loss with the ability to perceive sound. Generally, hearing loss may be conductive, sensorineural, or some combination of both conductive and sensorineural. Conductive hearing loss typically results from a dysfunction in any of the mechanisms that ordinarily conduct sound waves through the outer ear, the eardrum, or the bones of the middle ear. Sensorineural hearing loss typically results from a dysfunction in the inner ear, including the cochlea where sound vibrations are converted into neural signals, or any other part of the ear, auditory nerve, or brain that may process the neural signals.

Example hearing prostheses include traditional hearing aids, vibration-based hearing devices, cochlear implants, and auditory brainstem implants. A traditional hearing aid, which is an acoustic stimulation device, typically includes a small microphone to detect sound, an amplifier to amplify certain portions of the detected sound, and a speaker to transmit the amplified sounds into the person's ear canal.

A vibration-based hearing device, which is also an acoustic stimulation device, typically includes a microphone to detect sound and a vibration mechanism to apply mechanical vibrations corresponding to the detected sound directly to a person, thereby causing vibrations in the person's inner ear. Vibration-based hearing devices include, for example, bone conduction devices, middle ear devices, and direct acoustic cochlear stimulation devices. A bone conduction device transmits vibrations corresponding to sound via the teeth and/or skull. A so-called middle ear device transmits vibrations corresponding to sound via the middle ear (i.e., the ossicular chain), without using the teeth or skull. A direct acoustic cochlear stimulation device transmits vibrations corresponding to sound via the inner ear (i.e., the cochlea), without using the teeth, skull or middle ear.

A cochlear implant provides a person with the ability to perceive sound by stimulating the person's auditory nerve via an array of electrodes implanted in the person's cochlea. A microphone coupled to the cochlear implant detects sound waves, which are converted into a series of electrical stimulation signals that are delivered to the implant recipient's cochlea via the array of electrodes. An auditory brainstem implant may use technology similar to a cochlear implant, but instead of applying electrical stimulation to a person's cochlea, the auditory brainstem implant applies electrical stimulation directly to a person's brain stem, bypassing the cochlea altogether. Electrically stimulating auditory nerves in a cochlea with a cochlear implant or electrically stimulating a brainstem may enable persons with hearing loss to perceive sound.

Further, some persons may benefit from a hearing prosthesis that combines two or more characteristics of the traditional hearing aids, vibration-based hearing devices, cochlear implants, or auditory brainstem implants (e.g., two or more modes of stimulation) to enable the person to perceive sound. Such hearing prostheses can be referred to as bimodal hearing prostheses. Still other persons benefit from two hearing prostheses, one for each ear (e.g., a so-called binaural system generally or a bilateral system for persons with two cochlear implants).

SUMMARY

The effectiveness of a hearing prosthesis depends on the design of the prosthesis itself and on how well the prosthesis is configured for or fitted to a prosthesis recipient. The fitting of the prosthesis, sometimes also referred to as mapping, creates a set of configuration settings and other data, sometimes also referred to as a program, that define the specific characteristics of the signals (acoustic, mechanical vibration, and/or electrical) delivered to relevant portions of the person's outer ear, middle ear, inner ear, auditory nerve, and facial/skull structures. The configuration or program may also include a prescription rule that defines a relationship between audio input parameters and output parameters for one or more audio frequency channels of the hearing prosthesis.

A conventional hearing prosthesis is configured to operate according to one or more programs that are commonly optimized by an audiologist or clinician during the fitting process for speech understanding or intelligibility (e.g., an optimized program or programs). In the present disclosure, the hearing prosthesis is also configured to operate according to other programs. These other programs may not be optimized for speech intelligibility, but still provide acceptable speech intelligibility. Conventional hearing prostheses commonly avoid or otherwise omit such non-optimized programs, because hearing prosthesis recipients may perceive these non-optimized programs as not sounding as good as the optimized program. In contrast, the present disclosure uses such non-optimized programs to improve overall functioning of the hearing prosthesis. For instance, a program may deliver similar/equivalent speech intelligibility to the optimized program, but require less battery power and/or generate less heat in the hearing prosthesis.

In one example, a hearing prosthesis conserves a power supply by shifting (e.g., downshifts) from operating according to a first program (e.g., an optimized program) to a second program that requires less battery power yet provides similar or acceptable speech performance. Generally, different programs may be characterized by changing processing strategies and/or parameters that affect power consumption. In this example, the downshift occurs when a sensor (e.g., an incorporated or otherwise communicatively coupled sensor) that is configured to monitor a remaining charge level of a power supply provides data that is indicative of the remaining charge or power level approaching or crossing one or more thresholds.

In another example, a hearing prosthesis helps to maintain an appropriate operating temperature by shifting from operating according to a first program to a second program that generates less heat in the hearing prosthesis. Generally, different programs may be characterized by changing processing strategies and/or parameters that affect power consumption and heat generation. In this example, the program shift occurs when a temperature sensor provides data that is indicative of the temperature of the hearing prosthesis approaching or crossing one or more thresholds. The temperature sensor may be employed in isolation or in conjunction with the charge level sensor to shift programs or otherwise adjust operating parameters that affect heat generation and power consumption.

Various aspects and examples are described herein as being implemented by methods, systems (such as, a hearing prosthesis system), and/or programming in the form of a non-transitory computer-readable medium for automated (e.g., without direct user input) or non-automated program shifting.

DETAILED DESCRIPTION

The following detailed description describes various features, functions, and attributes with reference to the accompanying figures. In the figures, similar symbols typically identify similar components, unless context dictates otherwise. The illustrative embodiments described herein are not meant to be limiting. Certain features, functions, and attributes disclosed herein can be arranged and combined in a variety of different configurations, all of which are contemplated in the present disclosure. For illustration purposes, some features and functions are described with respect to medical devices, such as hearing prostheses. However, the features and functions disclosed herein may also be applicable to other types of devices, including other types of medical and non-medical devices.

Figure 1:
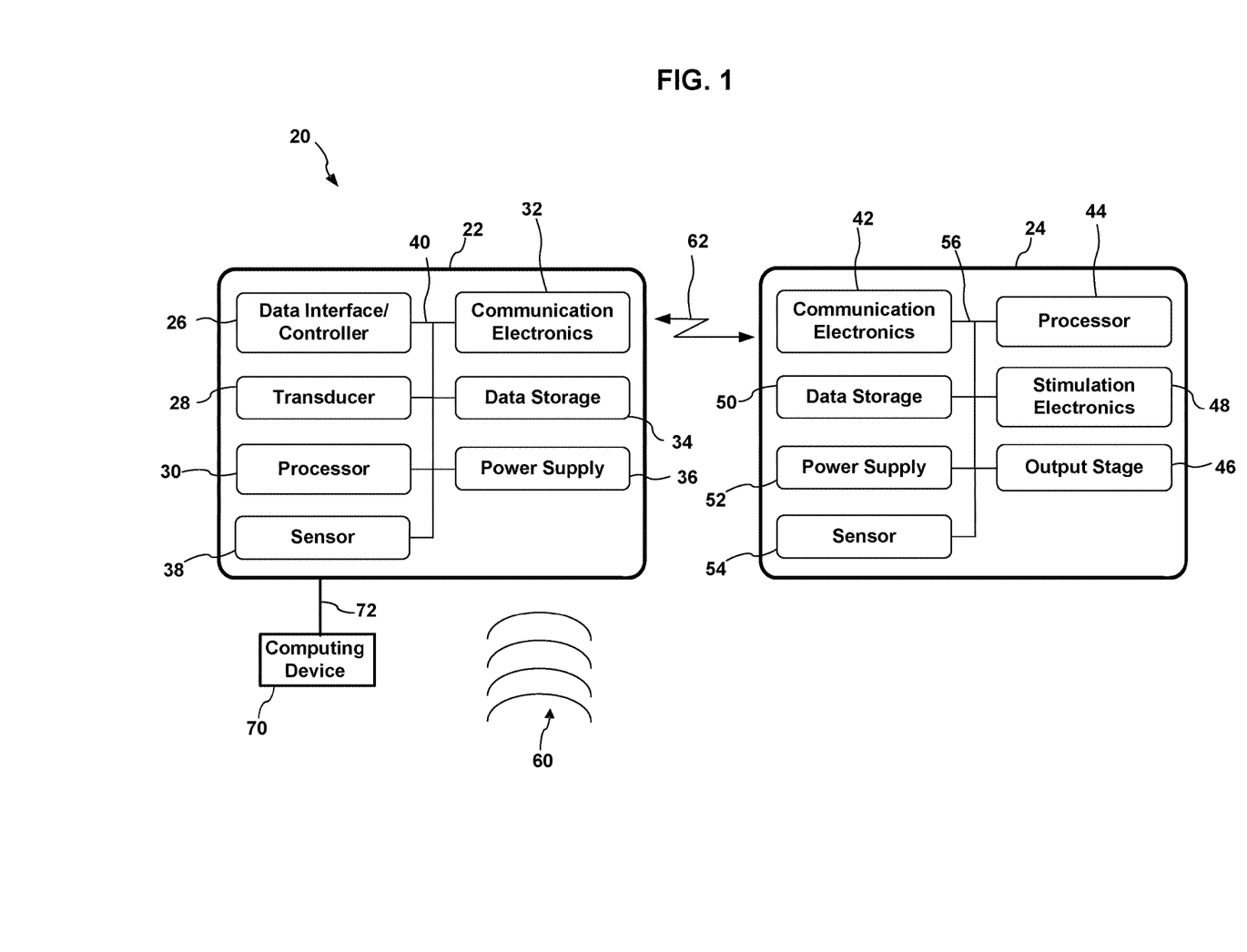
FIG. 1 illustrates a block diagram of a hearing prosthesis system according to an embodiment of the present disclosure.

Referring now to FIG. 1, an example electronic device or system 20 includes a first component 22 and a second component 24. The device 20 may be a hearing prosthesis, such as a cochlear implant, a traditional hearing aid, a bone conduction device, a direct acoustic cochlear stimulation device, an auditory brainstem implant, a bimodal hearing prosthesis, a middle ear stimulating device, or any other type of hearing prosthesis configured to assist a prosthesis recipient to perceive sound.

In this context, the first component 22 can be generally external to a recipient and communicate with the second component 24, which can be implanted in the recipient. In other examples, the components 22, 24 can both be at least partially implanted or can both be at least partially external to the recipient. In yet other examples, the first and second component 22, 24 may be combined into a single operational component or device. In such examples, the single unit (i.e., combined first component 22 and second component 24) may be totally implanted. Generally, an implantable component or device can be hermetically sealed and otherwise adapted to be at least partially implanted in a person.

In FIG. 1, the first component 22 includes a data interface 26 (such as a universal serial bus (USB) controller), one or more transducers or microphones 28, one or more processors or controllers 30 (such as digital signal processors (DSPs)), communication electronics 32 (such as an electromagnetic radio frequency (RF) transceiver), data storage 34, a power supply 36, and one or more sensors 38, all of which may be coupled directly or indirectly via a wired conductor or wireless link 40. In the example of FIG. 1, the second component 24 includes communication electronics 42 (such as another RF transceiver), one or more processors or controllers 44, an output amplifier stage or circuit 46, stimulation electronics 48, data storage 50, a power supply 52, and one or more sensors 54 all of which may be coupled directly or indirectly via a wired conductor or wireless link 56.

Generally, the transducer(s) or microphone(s) 28 are configured to receive external audible sounds 60. Further, the microphone may include combinations of one or more omnidirectional or directional microphones configured to receive background sounds and/or to focus on sounds from a specific direction, such as generally in front of the prosthesis recipient. Alternatively or in addition, the transducer 28 may include telecoils or other sound transducing components that receive sound and convert the received sound to electronic signals. Further, the device 20 may be configured to receive sound information from other sound input sources, such as electronic sound information received through the data interface 26 and or the communication electronics 32.

In one example, the processor 30 of the first component 22 is configured to process, amplify, encode, or otherwise convert the audible sounds 60 (or other electronic sound information) into encoded electronic signals that include audio data representing sound information, and to apply the encoded electronic signals to the communication electronics 32. In the present example, the communication electronics 32 of the first component 22 are configured to transmit the encoded electronic signals as electronic output signals 62 to the communication electronics 42 of the second component 24. Illustratively, the communication electronics 32, 42 can include magnetically coupled coils that establish an RF link between the units 22, 24. Accordingly, the communication electronics 32 can transmit the output signals 62 encoded in a varying or alternating magnetic field over the RF link between the components 22, 24.

The processor 44 is configured to decode the received output signals 62 and extract the encoded electronic signals. The second component 24 can then apply the encoded electronic signals to the output stage 46, which is configured to amplify the encoded electronic signals, as needed, and apply the amplified encoded electronic signals to the stimulation electronics 48. The stimulation electronics 48 use the applied amplified electronic signals to generate an output that allows a recipient to perceive the encoded electronic signals as sound. In the present example, the stimulation electronics 48 may include a transducer or actuator that provides auditory stimulation to the recipient through one or more of electrical nerve stimulation, audible sound production, or mechanical vibration of the cochlea, for example.

Generally, the processors 30, 44 are configured to convert the audible sounds or other electronic sound information into the encoded electronic signals in accordance with configuration settings or data for a prosthesis recipient. Generally, the configuration settings allow a hearing prosthesis to be configured for or fitted to a particular recipient. These configuration settings can be stored in the data storage 34, 50, for example.

Illustratively, the configuration settings include sound processing strategies that are implemented by the processor 30 to generate the encoded electronic signals from the audible sounds or other electronic sound information. For encoded electronic signals that are applied to cochlear implant components and, more particularly, to a cochlear electrode array implanted in a recipient, the stimulation data can define one or more of an intended electrode, mode of stimulation, stimulation amplitude, and stimulation duration. Thus, the encoded electronic signals can be used to control the timing and intensity of auditory stimulation pulses that are applied to a recipient by the stimulation electronics 48.

Generally, sound processing strategies include, but are not limited to, Continuous Interleaved Sampling (CIS), Spectral PEAK Extraction (SPEAK), Advanced Combination Encoders (ACE), Fundamental Asynchronous Stimulus Timing (FAST), Simultaneous Analog Stimulation, MPS, Paired Pulsatile Sampler, Quadruple Pulsatile Sampler, Hybrid Analog Pulsatile, n-of-m, and HiRes. More particularly, SPEAK is a low rate strategy that can operate within the 250-500 Hz range, ACE is a combination of CIS and SPEAK, and FAST. Other proprietary and non-proprietary sound processing strategies are included. The operation of these algorithms provides information on a stimulation mode (e.g., monopolar or bipolar electrode), a target electrode(s), and an amplitude of stimulation pulse(s), for example.

The configuration settings for acoustic hearing aids can include prescription rules for defining parameters, such as gain and maximum power output (MPO) levels or settings, from the hearing prosthesis recipient's audiogram and maximum comfort levels across a range of frequencies. Generally, the audiogram is a graph of the audible thresholds for a range of frequencies. In some cases, the audiogram is defined by measured threshold levels across the recipient's residual hearing range. If a recipient specific audiogram is unavailable, a population average audiogram can also be used with the prescription rule to fit traditional hearing aid components of the hearing prosthesis.

Generally, prescription rules are specialized mathematical models or algorithms for calculating optimal gain settings so that external sounds are perceived by a hearing prosthesis recipient intelligibly and at similar loudness that the external sounds would be perceived by a normal-hearing person. Prescription rules typically focus on making speech intelligible and reducing background noise. Some prescription rules are non-linear and apply different gain settings for different frequencies or frequency bands to provide a more fine-tuned hearing prosthesis fitting for the recipient. Example prescription rules include, but are not limited to, National Acoustic Laboratories' (NAL) prescriptions rules (including NAL-R, NAL-RP, NAL-NL2, etc.), the Desired Sensation Level (DSL) prescription rule, and the Cochlear Hybrid Prescription Rule (CHP). Other proprietary and non-proprietary prescription rules are also possible.

Referring back to the power supplies 36, 52, each power supply provides power to various components of the first and second components 22, 24, respectively. In another variation of the system 20 of FIG. 1, one of the power supplies may be omitted, for example, the system may include only the power supply 36 or the power supply 52, which is used to provide power to other components. The power supplies 36, 52 can be any suitable power supply, such as one or more non-rechargeable or rechargeable batteries. In one example, one or more of the power supplies 36, 52 are batteries that can be recharged wirelessly, such as through inductive charging. Generally, a wirelessly rechargeable battery facilitates complete subcutaneous implantation of a device to provide a fully or at least partially implantable prosthesis. A fully implanted hearing prosthesis has the added benefit of enabling the recipient to engage in activities that expose the recipient to water or high atmospheric moisture, such as swimming, showering, saunaing, etc., without the need to remove, disable or protect, such as with a water/moisture proof covering or shield, the hearing prosthesis. A fully implanted hearing prosthesis also spares the recipient of stigma, imagined or otherwise, associated with use of the prosthesis.

Further, the data storage 34, 50 may be any suitable volatile and/or non-volatile storage components. The data storage 34, 50 may store computer-readable program instructions and perhaps additional data. In some embodiments, the data storage 34, 50 stores data and instructions used to perform at least part of the processes disclosed herein and/or at least part of the functionality of the systems described herein. Although the data storage 34, 50 in FIG. 1 are illustrated as separate blocks, in some embodiments, the data storage can be incorporated, for example, into the processor(s) 30, 44, respectively.

In addition, the sensor(s) 38, 54 include one or more conventional sensors configured to monitor an operating characteristic of the device. For example, the sensors may include a sensor configured to monitor an operating characteristic of the power supplies 36, 52, such as a remaining charge level of the power supplies measured as a percentage of full battery charge. The operating characteristic may also relate to a remaining power supply life measured in time.

Alternatively or in combination, the sensor(s) 38, 54 include a conventional temperature sensor configured to monitor an operating temperature of the components 22, 24. The temperature sensor may be an in-situ temperature sensor that is configured to provide real-time data regarding temperature characteristics of the component(s) when operational. The temperature characteristics include instantaneous temperatures and/or temperature averages over time. Further, the temperature characteristics may be associated with internal temperature characteristics within the components, and/or with external temperature characteristics in areas adjacent and external to the components. In the present disclosure, monitoring temperature characteristics and responsively controlling operation of the components helps to maintain the operating temperature of the components within safe and/or comfortable temperature ranges. Maintaining the operating temperature within such ranges may be particularly important for devices that are in contact with the skin of a user, or that are at least partially implanted under the skin of the user. In addition, maintaining the operating temperature within given ranges may help to prolong the operational life of the components.

The system 20 illustrated in FIG. 1 further includes a computing device 70 that is configured to be communicatively coupled to the hearing prosthesis 22 via a connection or link 72. The link 72 may be any suitable wired connection, such as an Ethernet cable, a Universal Serial Bus connection, a twisted pair wire, a coaxial cable, a fiber-optic link, or a similar physical connection, or any suitable wireless connection, such as BLUETOOTH, WI-FI, WiMAX, inductive or electromagnetic coupling or link, and the like.

In general, the computing device 70 and the link 72 are used to operate the hearing prosthesis in various modes. In one example, the computing device and the link are used to adjust various parameters of the hearing prosthesis. The computing device and the link can also be used to load a recipient's configuration settings on the hearing prosthesis such as via the data interface 26. In another example, the computing device and the link are used to upload other program instructions and firmware upgrades to the hearing prosthesis. In yet other examples, the computing device and the link are used to deliver data (e.g., sound information) and/or power to the hearing prosthesis to operate the components thereof and/or to charge a power supply. Still further, various other modes of operation of the prosthesis can be implemented by utilizing the computing device and the link.

The computing device 70 can further include various additional components, such as a processor, a storage device, and a power source. Further, the computing device can include user interface or input/output devices, such as buttons, dials, a touch screen with a graphic user interface, and the like, that can be used to turn the prosthesis on and off, adjust the volume, adjust or fine tune the configuration data or parameters, etc. Thus, the computing device can be utilized by the recipient or a third party, such as a guardian of a minor recipient or a health care professional, to control or adjust the hearing prosthesis.

Various modifications can be made to the device 20 illustrated in FIG. 1. For example, a user interface or input/output devices can be incorporated into the first component 22 and/or the second component 24. In another example, the second component 24 can include one or more microphones or transducers. Generally, the device 20 may include additional or fewer components arranged in any suitable manner. In some examples, the device 20 may include other components to process external audio signals, such as components that measure vibrations in the skull caused by audio signals and/or components that measure electrical outputs of portions of a person's hearing system in response to audio signals.

Figure 2:
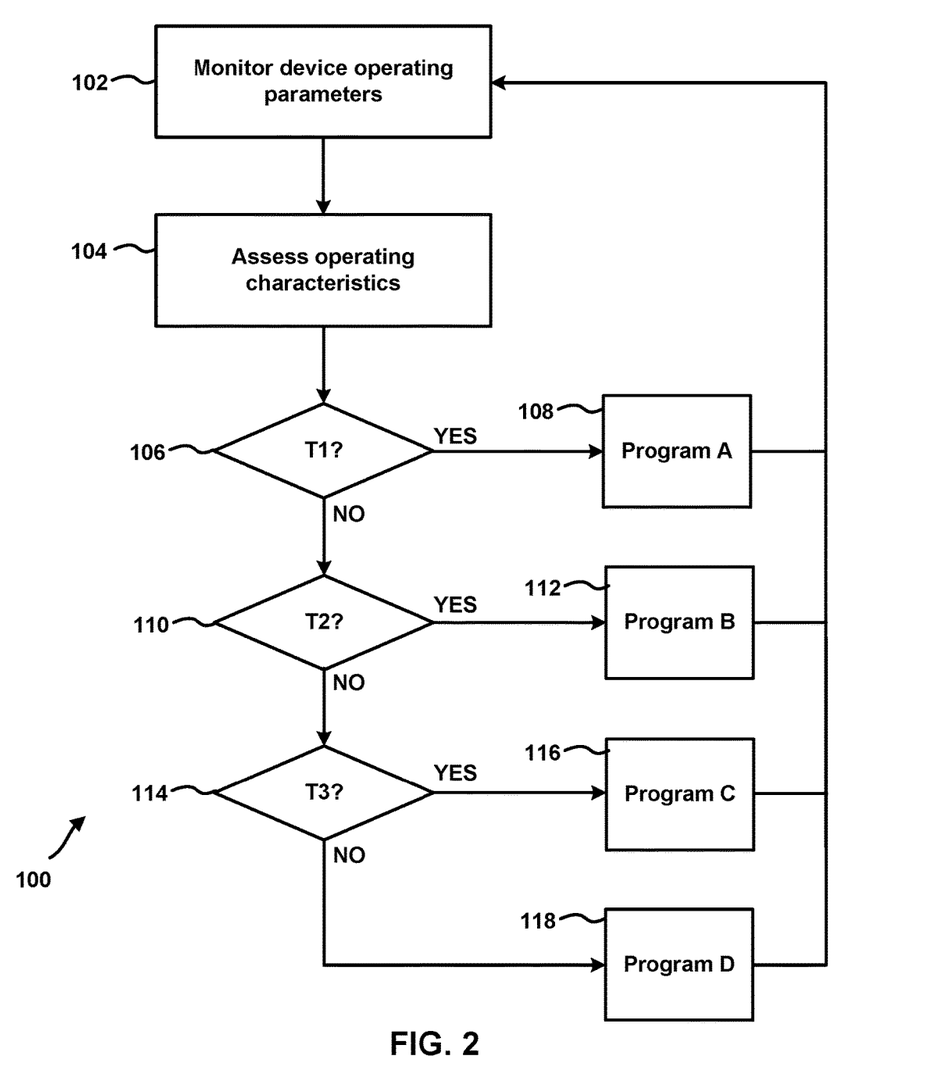
FIG. 2 is a flowchart showing a method or algorithm for controlling a hearing prosthesis.

Referring now to FIG. 2, an example method 100 is illustrated, which can be implemented by the system of FIG. 1, for instance. Generally, the method 100 may include one or more operations, functions, or actions as illustrated by one or more of blocks 102-118. Although the blocks 102-118 are illustrated in a particular order, these blocks may also be performed in a different order than illustrated, and some blocks may even be omitted and other blocks may be added according to certain implementations.

In addition, each block 102-118 may represent a module, a segment, or a portion of program code, which includes one or more instructions executable by a processor for implementing specific logical functions or steps in the process. The program code may be stored on any type of computer readable medium or storage device including a disk or hard drive, for example. The computer readable medium may include non-transitory computer readable medium, such as computer-readable media that stores data for short periods of time like register memory, processor cache, and Random Access Memory (RAM). The computer readable medium may also include non-transitory media, such as secondary or persistent long term storage, like read only memory (ROM), optical or magnetic disks, compact-disc read only memory (CD-ROM), etc. The computer readable media may also include any other volatile or non-volatile storage systems. The computer readable medium may be considered a computer readable storage medium, for example, or a tangible storage device. In addition, one or more of the blocks 102-118 may represent circuitry that is wired to perform the specific logical functions of the method 100.

In FIG. 2, at block 102, a computing device (e.g., one or more of the processors 30, 44 or the computing device 70) monitors operating parameters or characteristics of a device or system (e.g., the device 20). In one example, at block 102, the device is operating in a first mode, and a processor uses one or more sensors 38, 54 to record previous and/or monitor current operating characteristics, such as charge levels of a power supply that is configured to provide power to the device. Alternatively or in combination, at block 102, the operating characteristics include temperature characteristics of the device.

At block 104, the processor assesses the operating parameters or characteristics of the device or system. For example, the processor determines a power supply life or remaining charge level for operating the device according to one or more programs. In another example, the processor determines whether the device is operating within an acceptable temperature range. In this example, the processor also accounts for spikes or increases in the temperature that are unrelated to the operation of the device by monitoring the instantaneous and long term battery consumption of the device to account for environmental (external) influences on the temperature.

Blocks 106-118 illustrate an example process for shifting the operating program in response to the operating parameters or characteristics. At block 106, the processor determines whether one or more operating parameters meet a first threshold T1. If the operating parameter(s) meet the threshold T1, control passes to block 108 and the processor operates the device according to a program A. If the operating parameter(s) do not meet the threshold T1, control passes to block 110, and the processor determines if the operating parameter(s) meet a second threshold T2. If the operating parameter(s) meet the threshold T2, control passes to block 112 and the processor operates the device according to a program B. If the operating parameter(s) do not meet the threshold T2, control passes to block 114, and the processor determines if the operating parameter(s) meet a third threshold T3. If the operating parameter(s) meet the threshold T3, control passes to block 116 and the processor operates the device according to a program C. If the operating parameter(s) do not meet the threshold T3, control passes to block 118, and the processor operates the device according to a program D. Control flows from blocks 108, 112, 116, 118 back to block 102 to continue monitoring the operating parameter(s).

Generally, operating the device according to the program A consumes more power than the program B, operating the device in the program B consumes more power than the program C, operating the device in the program C consumes more power than the program D, and so forth if there are additional programs. In the example of the device being a hearing prosthesis, the programs are associated with hearing prosthesis programs as described herein, and each lower power program still provides acceptable speech performance or intelligibility.

According to one aspect, shifting between different programs is performed according to a transfer function that provides a relatively smooth transition between different programs. Illustratively, a transition from a first program to a second program may include altering parameters from a first set of parameters to a second set of parameters; the first and second sets of parameters being associated with the first and second programs, respectively. In one example, the transition from the first program to the second program is performed by linking a power characteristic of the battery (e.g., a battery voltage) to a transfer function, which in turn drives changes from the first set of parameters to the second set of parameters. Generally, the power characteristic of the battery varies fairly gradually over time, such that linking the changes from the first to the second set of parameters to the power characteristic results in the smooth transition between different programs.

Further, at one or more of blocks 108, 112, 116, or 118, a notification may be provided (such as a visual notice, an audible alert, and/or a tactile indication) that the device is switching to a different program. In one example, different notifications are provided when the device switches to different programs. For instance, one audible tone may be provided when switching from program A to program B, two audible tones may be provided when switching from program B to program C, and three audible tones may be provided when switching from program C to program D.

The shift to a different program can be automatic and not require any direct user input, or the shift can require a user input to confirm or authorize the program shift. In one example, after the notification is provided and before the program shift is performed, a user input may be received through a user interface to thereby confirm and perform the program shift. In another example, the user provides an initial input through a user interface that functions to authorize the computing device to perform thereafter automatic shifts between different programs. Such an initial input functions generally as an opt-in authorization to allow the computing device to monitor operating characteristics, and to shift responsively between programs without requiring a further user input to confirm each program shift.

Referring back to blocks 106-118, in one illustrative example, a hearing prosthesis is being operated according to program A, and when the charge level remains above about a 30% remaining charge level (first threshold T1 at block 106), the hearing prosthesis continues operation according to program A (block 108). When the charge level is less than the 30% remaining charge level but greater than about a 20% remaining charge level (second threshold T2 at block 110), the hearing prosthesis shifts from program A to program B (block 112). When the charge level is less than the 20% remaining charge level but greater than about a 10% remaining charge level (third threshold T3 at block 114), the hearing prosthesis shifts from the program B to program C (block 116). When the charge level falls below the 10% remaining charge level, the hearing prosthesis shifts from the program C to the program D (block 118).

In another aspect, the hearing prosthesis is configured to analyze power use and anticipate when the charge level is approaching one or more thresholds. In this case, the hearing prosthesis is configured to determine when to most efficiently shift programs, and may generally shift programs sooner than in other embodiments. In one example, a hearing prosthesis is being operated according to program A, and when the hearing prosthesis determines that there are over about two hours of battery life remaining (first threshold T1 at block 106), the hearing prosthesis continues operation according to program A (block 108). When the hearing prosthesis determines that there are two hours of battery life remaining or that battery life is predicted to quickly approach the two-hour level (second threshold T2 at block 110), the hearing prosthesis shifts from program A to program B (block 112). In this example, hearing prosthesis determines that the remaining battery life is nearing about one hour (the third threshold T3 at block 114), and the hearing prosthesis responsively shifts from program B to program C (block 116). In one example, the third threshold T3 includes a remaining battery life range that is nearing or greater than one hour (e.g., 70 minutes) and down to about thirty minutes. When the hearing prosthesis determines that the remaining battery life is nearing thirty minutes, the hearing prosthesis responsively shifts from program C to program D (block 118).

As discussed above, operating the hearing prosthesis according to the program A consumes more power than the program B, which in turn consumes more power than the program C, which in turn consumes more power than the program D, and so forth if there are additional programs. In one example, the decrease in power consumption corresponds to a reduction in heat generated in the hearing prosthesis. In this example, the program shifting can be performed to help to control an operating temperature of the device. Referring to FIG. 2, in the present example, a hearing prosthesis is being operated according to program A, and when the operating temperature is less than about 35° C. (first threshold T1 at block 106), the hearing prosthesis continues operation according to program A (block 108). When the operating temperature is greater than 35° C. but less than about 37° C. (second threshold T2 at block 110), the hearing prosthesis shifts from program A to program B (block 112). When the operating temperature is greater than 37° C. but less than about 39° C. (third threshold T3 at block 114), the hearing prosthesis shifts from the program B to program C (block 116). When operating temperature is greater than 39° C., the hearing prosthesis shifts from the program C to the program D (block 118).

Additional or fewer thresholds, other threshold types, and/or other threshold values may be used in other examples. Generally, the thresholds may be parameters that a clinician can set on the hearing prosthesis. Alternatively or in combination, a program shifting algorithm or process utilizes parameters that are not accessible to the clinician. Such parameters may relate to either specific algorithms or inner working of a signal path.

Further, according to the example of FIG. 2, the computing device is also configured to automatically shift from operating according to a less optimal program, which may be associated with a lower power consumption or lower heat generation, to a more optimal program, which may be associated with greater power consumption or heat generation. For instance, at one point the hearing prosthesis may be operating according to program B, and when control passes back through blocks 102-106, the processor determines that the charge level is increasing and is above the 30% threshold. In this example, the processor responsively shifts from program B back to program A (block 108). In another similar example, at one point the hearing prosthesis may be operating according to program B, and when control passes back through blocks 102-106, the processor determines that the operating temperature is decreasing and is less than the 35° C. threshold. In response, the processor similarly shifts from program B back to program A (block 108).

As discussed above, different programs (e.g., programs A-D) are generally characterized by different power consumption and/or heat generation characteristics. In the present disclosure, various configuration settings or operational variables that can be modified to alter such power consumption and heat generation characteristics. In the example of hearing prosthesis programs, some of these configuration settings or operational variables include signal processing strategies, stimulation rate, FM or powered antenna range, maximum comfort levels, noise processing and reduction, user voice filtering, microphone directivity, and the like.

Referring to the signal processing strategy, a program may utilize a default speech processing strategy, such as ACE, which does not utilize perceptual coding concepts. In contrast, another program may utilize psychophysical sound processing strategies that do utilize perceptual coding concepts. Perceptual coding concepts take into account the fact that some sounds are perceptually masked by other sounds (the masking phenomena), and therefore need not be presented as audio stimulation components. Masking functionally results in fewer spectral components (or maxima) that need be encoded, thereby mitigating power demands on a processor. Psychophysical sound processing strategies use masking models to estimate effects of the masking phenomena on a recipient, and in turn, to process and encode received sound information into corresponding encoded electronic signals that may omit sounds that would be perceptually masked.

Figure 3:
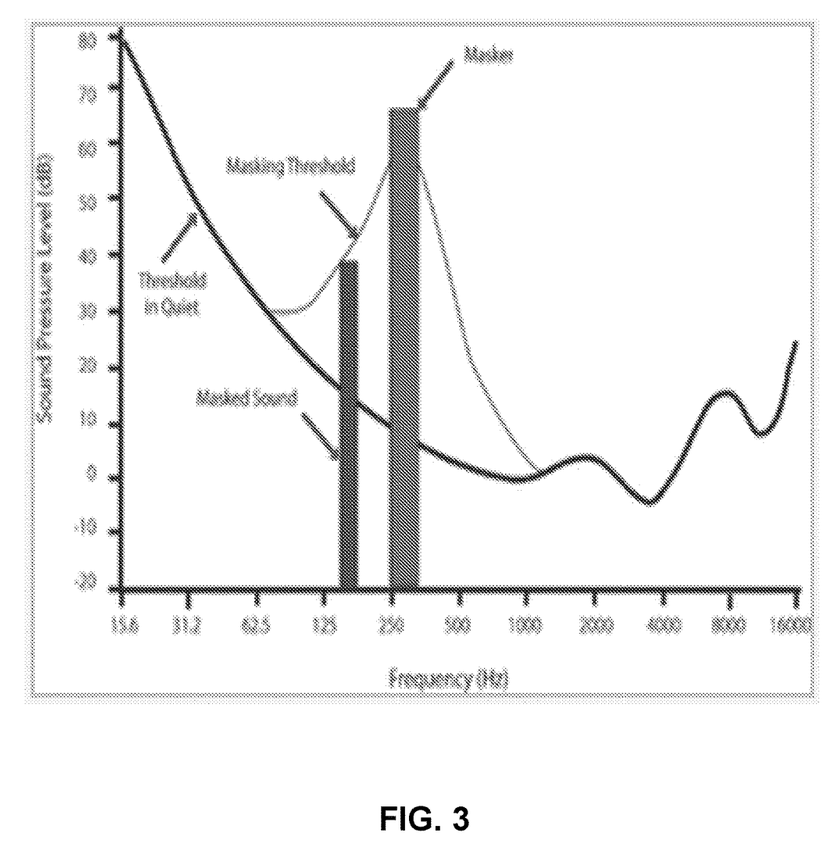
FIG. 3 illustrates the effects of a masker or masking sound on other sounds.

In the present disclosure, the masking models used by psychophysical sound processing strategies can depend in part on sound intensity parameters. FIG. 3 illustrates an example of a masking model, wherein a masker or masking sound (e.g., a nearby car horn) makes it difficult for a person to hear a masked sound (e.g., words that are whispered to the person). In this example, the louder sound masks the softer sound. However, the masking models contemplated herein are not only dependent on different sound intensities, but also on spectral and temporal characteristics as well. Such spectral and temporal characteristics may be defined in part by various adjustable parameters, such as spectral masking slopes, temporal masking offsets, and the number of spectral maxima.

Figure 4:
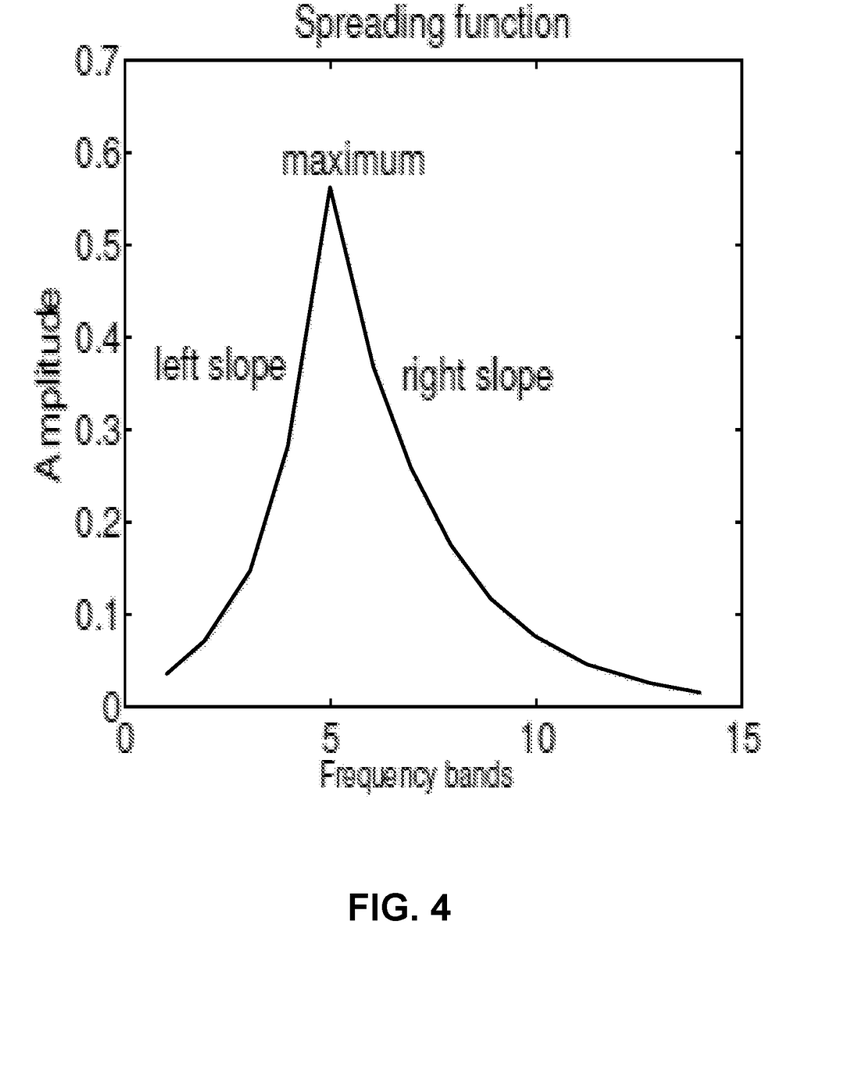
FIG. 4 illustrates an example of spectral masking slopes.

Spectral masking slope parameters describe how maskers impact sounds that are at either higher or lower frequencies. FIG. 4 illustrates an example of how a left or low frequency slope, and a right or high frequency slope may be defined with respect to a given maxima (see also FIG. 3 and how the masking slope defines a masking threshold). Generally, a relatively more aggressive masking slope corresponds to a more gradual (or less steep slope), which in turn functions to eliminate more maxima from being encoded and provides a greater degree of masking.

Referring to temporal masking offsets, masking can also have either forward or backward impact. Forward masking occurs when the sound following a masker cannot be heard, and backward masking occurs when a masker follows the sound. A forward masker generally impacts sound thresholds approximately 100-200 ms following the masker, and a backward masker generally impacts sound thresholds approximately 10 ms prior to the masker. Greater temporal masking offsets generally help to reduce power consumption and heat generation, as compared with lesser temporal masking offsets. For instance, a forward masking offset of 150-250 ms is greater than a forward masking offset of 100-200 ms, and a backward masking offset of 15 ms is greater than a backward masking offset of 10 ms.

Regarding the number of spectral maxima, taking into account perceptual coding concepts benefits from fewer maxima as less signal processing is required. It is also possible to artificially limit the number of maxima in programs that utilize psychophysical sound processing strategies, as well as, in programs that do not. Fewer maxima results in less stimulation, and thus less required power. However, it should be noted that fewer stimulatory maxima will result in a quieter overall program, because not as many stimulatory components are involved in loudness summation.

Programs that utilize psychophysical sound processing strategies, and programs that do not, may also have different power consumption and/or heat generation characteristics by modifying the stimulation rate. Reducing the stimulation rate, similar to reducing the number of spectral maxima, results in reduced power consumption.

Making adjustments to communication systems may also affect power consumption in programs that utilize psychophysical sound processing strategies, and programs that do not. For instance, the device may include an FM system that includes a power antenna (e.g., part of the data interface 26 and/or the communication electronics 32, 42), and power consumption can be based on the operational range of the FM system. Accordingly, limiting the range of the FM system reduces the power supplied thereto and the power consumption of the device.

Modifying the necessary RF power level is another option to alter power consumption characteristics in programs that utilize psychophysical sound processing strategies, and programs that do not. In one example, a processor calculates highest voltage electrodes (e.g., cochlear electrodes) and modifies the hearing comfort level on the highest demand electrodes, which in turn lowers the compliance limit or implant voltage. This approach lowers the perceived sound level at no significant cost to speech intelligibility if reductions are conducted within an acceptable limit. This approach may be performed in addition to or alternatively with utilizing perceptual coding concepts.

In another example, different programs may also have different power consumption and/or heat generation characteristics based on the aggressiveness or degree of noise reduction (on one or more hearing prosthesis channels). Generally, noise reduction techniques are utilized to reduce the number of spectral peaks required for data encoding. In a further example, different programs may include user voice filtering, which uses a sound processor to detect a user's own voice and responsively refrain from encoding the user's own voice (or otherwise encode less of the user's own voice). User voice filtering can also help to reduce power consumption. In yet another example, varying degrees of microphone directivity can be used to filter out ambient noise that does not need to be encoded, which can further help to reduce power consumption.

The following Table 1 provides some example parameters and characteristics for the different programs A-D described above:

TABLE 1

|  | Signal Processing Strategy | Spectral Masking Slopes | Temporal Masking Offset | No. of Spectral Maxima | Stimulation Rate | FM Range |
| --- | --- | --- | --- | --- | --- | --- |
| Program A | ACE | None | None | Standard (e.g. 8) | Clinical rate (e.g. 900 pps) | Standard (about 50 meters) |
| Program B | ACE | None | None | Fewer (e.g. 6) | Modified Clinical rate (e.g. 700 pps) | 2/3 standard (30 meters) |
| Program C | ACE with psychophysical sound processing | Lo-freq: modest Hi-freq: aggressive | Forward: 100 ms Backward: none | Fewer (e.g. 4) | Slower rate (e.g. 500 pps) | 1/3 standard (15 meters) |

TABLE 1-continued

| | Signal Processing Strategy | Spectral Masking Slopes | Temporal Masking Offset | No. of Spectral Maxima | Stimulation Rate | FM Range |
|---|---|---|---|---|---|---|
| Program D | ACE with psychophysical sound processing | Lo-freq: aggressive Hi-freq: aggressive | Forward: 250 ms Backward: 10 ms | Fewer (e.g. 2) | Slower rate (e.g. 400 pps) | 1/6 standard (8 meters) |

Figure 5:
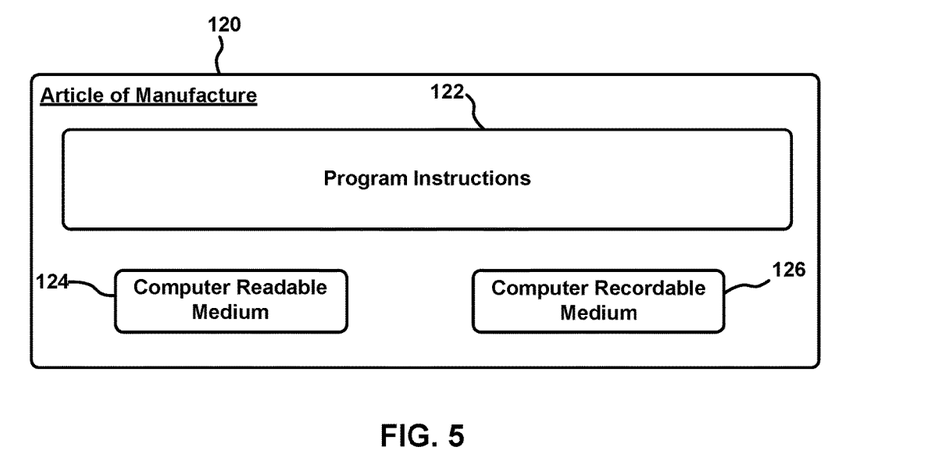
FIG. 5 is a block diagram of an article of manufacture including computer-readable media with instructions for controlling a hearing prosthesis.

FIG. 5 shows an example of an article of manufacture 120 including computer readable media with instructions 122 for program shifting of a device. In FIG. 5, the example article of manufacture 120 includes computer program instructions 122 for executing a computer process on a computing device, arranged according to at least some embodiments described herein, such as the method 100 of FIG. 2.

In some examples, the article of manufacture 120 includes a computer-readable medium 124, such as, but not limited to, a hard disk drive, a Compact Disc (CD), a Digital Video Disk (DVD), a digital tape, flash memory, etc. In some implementations, the article of manufacture 120 includes a computer recordable medium 126, such as, but not limited to, a hard disk drive, a Compact Disc (CD), a Digital Video Disk (DVD), a digital tape, flash memory, etc. The one or more programming instructions 122 include, for example, computer executable and/or logic implemented instructions. In some embodiments, a computing device such as the processor(s) 30, 44 and/or the computing device 70, alone or in combination with one or more additional processors or computing devices, may be configured to perform certain operations, functions, or actions to implement the features and functionality of the disclosed systems and methods based at least in part on the programming instructions 122.

While various aspects and embodiments have been disclosed herein, other aspects and embodiments will be apparent to those skilled in the art. The various aspects and embodiments disclosed herein are for purposes of illustration and are not intended to be limiting.

What is claimed is:

1. A method for operating a hearing prosthesis, comprising:
    operating the hearing prosthesis in accordance with a first program to process received sound signals and to generate stimulation output for delivery to a recipient of the hearing prosthesis based on the received sound signals;
    monitoring a temperature characteristic of the hearing prosthesis;
    determining that the temperature characteristic is at a threshold level; and
    responsive to determining that the temperature characteristic is at the threshold level, operating the hearing prosthesis in accordance with a second program to process received sound signals and to generate stimulation output for delivery to the recipient, wherein operating the hearing prosthesis in accordance with the second program generates less heat than operating the hearing prosthesis in accordance with the first program.

2. The method of claim 1, wherein operating the hearing prosthesis in accordance with the first program comprises:
    processing received sound signals using a first sound processing strategy that provides a first level of speech intelligibility to the recipient, and
wherein operating the hearing prosthesis in accordance with the second program comprises:
    processing received sound signals using a second sound processing strategy that provides a second level of speech intelligibility to the recipient that is less than the first level of speech intelligibility provided by the first sound processing strategy, wherein the second processing strategy generates less heat, when executed, than the first sound processing strategy.

3. The method of claim 2, wherein processing received sound signals using a first sound processing strategy comprises:
    processing received sound signals without utilizing a psychophysical sound processing strategy, and
wherein processing received sound signals using a second sound processing strategy, comprises:
    processing received sound signals with a psychophysical sound processing strategy.

4. The method of claim 2, wherein the first and second sound processing strategies are each psychophysical sound processing strategies, and wherein one or more of spectral masking slopes, temporal masking offsets, or the number of spectral maxima is different between the first and second sound processing strategies.

5. The method of claim 2, wherein operating the hearing prosthesis in accordance with the second program includes automatically operating the hearing prosthesis in the second program responsive to determining that the temperature characteristic is at the first threshold level.

6. The method of claim 1, wherein the threshold level is a first threshold level, and wherein the method further comprises:
    determining that the temperature characteristic is at a second threshold level; and
    responsive to determining that the temperature characteristic is at the second threshold level, operating the hearing prosthesis in accordance with a third program to process received sound signals and to generate stimulation output for delivery to the recipient of the hearing prosthesis,
    wherein operating the hearing prosthesis in accordance with the third program generates less heat than operating the hearing prosthesis in accordance with each of the first and second programs.

7. The method of claim 1, wherein the second program is characterized by use of a lower stimulation rate than in the first program.

8. The method of claim 1, wherein the second program is characterized by use of user voice filtering that is different than user voice filtering used in the first program.

9. The method of claim 1, wherein the second program is characterized by use of more aggressive noise reduction processing than used in the first program.

10. The method of claim 1, wherein the second program is characterized by use of one or more of a shorter operational range of an FM system of the hearing prosthesis than used in the first program or use of a reduced RF power level than used in the first program.

11. The method of claim 1, wherein the second program is characterized by use of microphone directivity that is different than the microphone directivity used in the first program.

12. A hearing prosthesis comprising:
a power supply configured to provide power to the hearing prosthesis;
at least one sensor configured to monitor a temperature characteristic of the power supply; and
a controller configured to:
operate the hearing prosthesis in a first mode to process received sound signals for output by the hearing prosthesis;
determine that the temperature characteristic is at a first threshold level;
responsive to determining that the temperature characteristic is at the first threshold level, automatically operate the hearing prosthesis in a second mode to process received sound signals for output by the hearing prosthesis, wherein operating the hearing prosthesis in the second mode generates less heat than operating the hearing prosthesis in the first mode.

13. The hearing prosthesis of claim 12, wherein:
to operate the hearing prosthesis in the first mode, the controller is configured to cause the hearing prosthesis to process received sound signals using a first sound processing strategy; and
to operate the hearing prosthesis in the second mode, the controller is configured to cause the hearing prosthesis to process received sound signals using a second sound processing strategy,
wherein the second processing strategy generates less heat, when executed, than the first sound processing strategy.

14. The hearing prosthesis of claim 13, wherein the second sound processing strategy is a psychophysical sound processing strategy, and wherein the first sound processing strategy is a non-psychophysical sound processing strategy.

15. The hearing prosthesis of claim 13, wherein the first and second sound processing strategies are each psychophysical sound processing strategies, and wherein one or more of spectral masking slopes, temporal masking offsets, or the number of spectral maxima is different between the first and second sound processing strategies.

16. The hearing prosthesis of claim 12, wherein the second mode is characterized by use of a lower stimulation rate than in the first mode.

17. The hearing prosthesis of claim 12, wherein the second mode is characterized by use of user voice filtering that is different than user voice filtering used in the first mode.

18. The hearing prosthesis of claim 12, wherein the second mode is characterized by use of more aggressive noise reduction processing than used in the first mode.

19. The hearing prosthesis of claim 12, wherein the second mode is characterized by use of one or more of a shorter operational range of an FM system of the hearing prosthesis than used in the first mode or use of a reduced RF power level than used in the first mode.

20. The hearing prosthesis of claim 12, wherein the second mode is characterized by use of microphone directivity that is different than the microphone directivity used in the first mode.

* * * * *